US008123726B2

(12) United States Patent  
Searfoss et al.

(10) Patent No.: US 8,123,726 B2  
(45) Date of Patent: Feb. 28, 2012

(54) LOW INSERTION FORCE HEMOSTASIS VALVE FOR VASCULAR INTRODUCER

(75) Inventors: Timothy Allen Searfoss, Palm Harbor, FL (US); Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 0 days.

(21) Appl. No.: 12/796,855

(22) Filed: Jun. 9, 2010

(65) Prior Publication Data

US 2010/0312190 A1 Dec. 9, 2010

Related U.S. Application Data

(60) Provisional application No. 61/268,154, filed on Jun. 9, 2009.

(51) Int. Cl.
*A61M 5/178* (2006.01)

(52) U.S. Cl. .................................. 604/167.04

(58) Field of Classification Search ............. 604/167.03, 604/167.04, 256
See application file for complete search history.

(56) References Cited

U.S. PATENT DOCUMENTS

| | | | |
|---|---|---|---|
| 4,610,665 A * | 9/1986 | Matsumoto et al. ..... | 604/167.04 |
| 4,626,245 A * | 12/1986 | Weinstein ................ | 604/167.04 |
| 4,798,594 A | 1/1989 | Hillstead | |
| 4,895,565 A * | 1/1990 | Hillstead ................. | 604/167.04 |
| 4,960,412 A * | 10/1990 | Fink ......................... | 604/167.04 |
| 5,000,745 A * | 3/1991 | Guest et al. ............. | 604/256 |
| 5,041,095 A | 8/1991 | Littrell | |
| 5,102,395 A * | 4/1992 | Cheer et al. ............. | 604/167.03 |
| 5,125,904 A | 6/1992 | Lee | |
| 5,176,652 A | 1/1993 | Littrell | |
| 5,267,966 A * | 12/1993 | Paul ......................... | 604/167.04 |
| 5,304,156 A | 4/1994 | Sylvanowicz et al. | |
| 5,409,463 A | 4/1995 | Thomas et al. | |
| 5,520,655 A | 5/1996 | Davila et al. | |
| 5,538,505 A | 7/1996 | Weinstein et al. | |
| 5,562,632 A | 10/1996 | Davila et al. | |
| 5,702,370 A | 12/1997 | Sylvanowicz et al. | |
| 6,663,599 B2 * | 12/2003 | Osbourne et al. ........ | 604/167.04 |
| 7,901,379 B2 * | 3/2011 | Argentine et al. ....... | 604/167.06 |
| 2004/0210194 A1 * | 10/2004 | Bonnette et al. ......... | 604/167.06 |
| 2006/0149294 A1 * | 7/2006 | Argentine et al. ............ | 606/108 |
| 2008/0097386 A1 | 4/2008 | Osypka | |
| 2009/0143739 A1 * | 6/2009 | Nardeo et al. ........... | 604/167.04 |
| 2010/0185153 A1 * | 7/2010 | Sugiki et al. ............. | 604/167.04 |
| 2010/0204655 A1 * | 8/2010 | Melsheimer ............. | 604/167.03 |

* cited by examiner

*Primary Examiner* — Nicholas Lucchesi  
*Assistant Examiner* — Aarti B Berdichevsky  
(74) *Attorney, Agent, or Firm* — Scott D. Wofsy; Edwards Wildman Palmer LLP

(57) ABSTRACT

A hemostasis valve for a vascular introducer includes a valve body having a seal region with opposed first and second end surfaces and a central axis extending through the seal region perpendicular to the first and second end surfaces. The first end surface of the seal region has a first grouping of cut lines formed on the first end surface and extending radially outward from the central axis. The second end surface of the seal region has a second grouping of cut lines formed on the second end surface and extending radially outward from the central axis. The first circumferential grouping of intersecting cut lines is axially aligned with and angularly offset from the second circumferential grouping of cut lines. A pair of planar slits extend angularly away from each cut line in the first end surface, through the valve body, to a respective pair of oppositely adjacent cut lines in the second end surface.

15 Claims, 6 Drawing Sheets

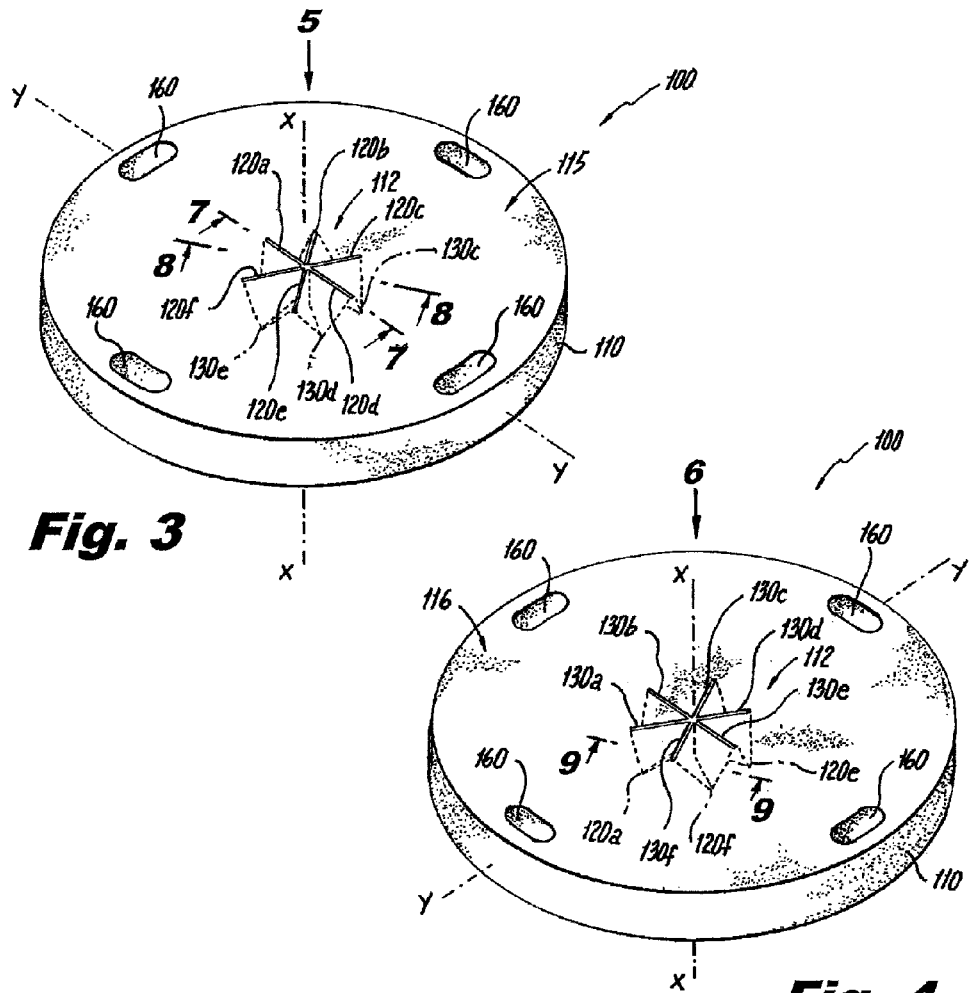
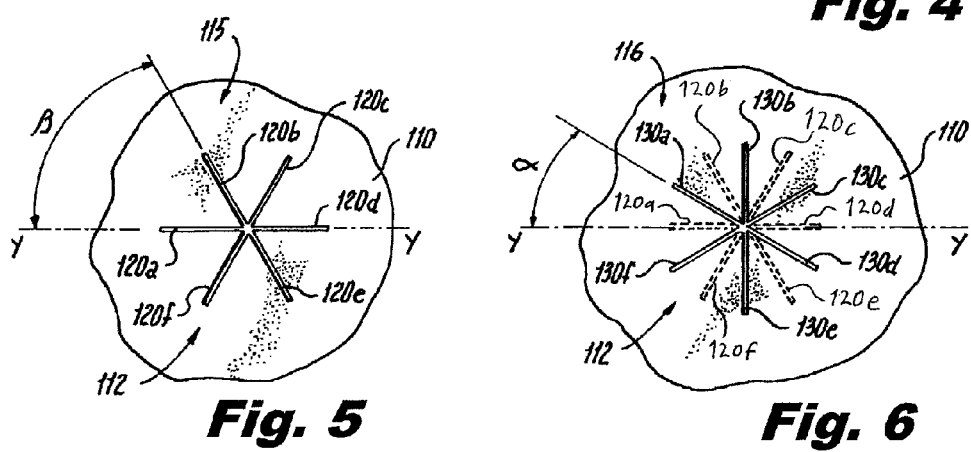
Fig. 3  Fig. 4
Fig. 5  Fig. 6

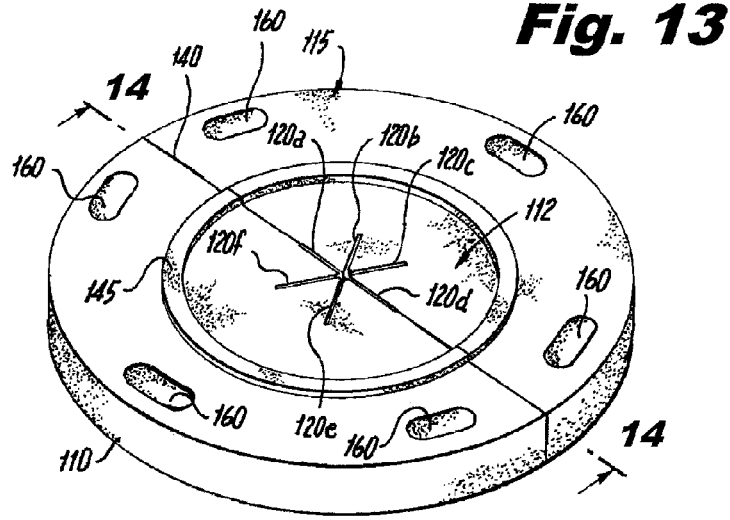
Fig. 13
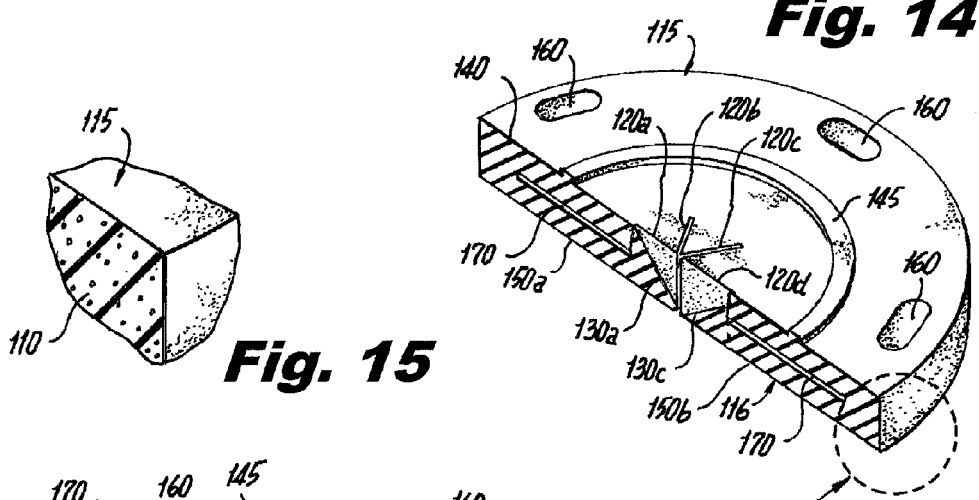
Fig. 14
Fig. 15
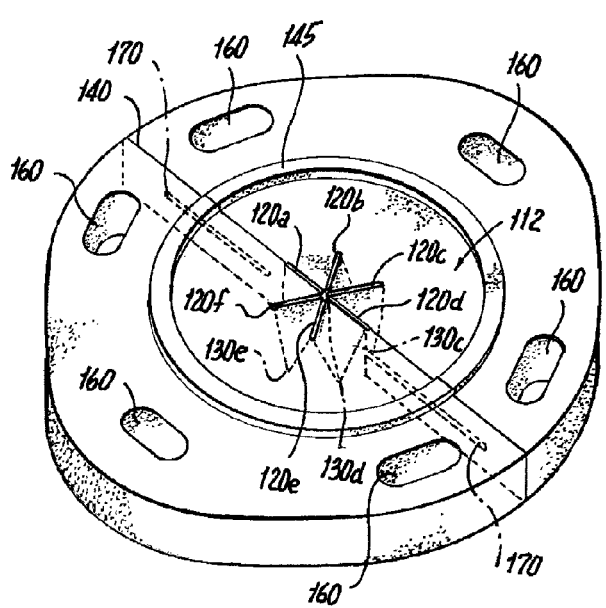
Fig. 16

LOW INSERTION FORCE HEMOSTASIS VALVE FOR VASCULAR INTRODUCER

CROSS-REFERENCE TO RELATED APPLICATIONS

This application claims priority to U.S. Provisional Patent Application No. 61/268,154, filed Jun. 9, 2009, which is incorporated herein by reference in its entirety.

BACKGROUND OF THE INVENTION

1. Field of the Invention

The subject invention is directed to vascular introducers, and more particularly, to a hemostasis valve for vascular introducers that provides a complete hemostatic seal regardless of the diameter of the object introduced through the valve, while exhibiting lower insertion and extraction forces than prior-art hemostasis valves.

2. Description of Related Art

The percutaneous introduction of diagnostic and therapeutic devices such as pacemaker leads and cardiovascular catheters into a blood vessel is typically accomplished with the aid of an introducer assembly. Introducer assemblies generally include a dilator having a tapered end portion and a thin-walled introducer sheath having a lumen extending through the sheath to initially accommodate the dilator, and subsequently accommodate the passage of a pacemaker lead or catheter.

Typically, the percutaneous introduction of an introducer assembly is accomplished by first inserting a needle into the blood vessel at a desired location and verifying its position by observing fluid return or by a similar method. While the needle is held firmly in place, a guidewire is inserted through the needle cannula to the desired depth. The guidewire is then held in place and the needle is withdrawn. Pressure is applied on the puncture site to minimize blood loss. Next, the introducer assembly is threaded over the guidewire. The introducer assembly is grasped close to the skin surface and advanced through the tissue to the desired position. Then, the dilator and guidewire are removed, leaving the sheath installed. A lead, catheter, or similar diagnostic or therapeutic device is then introduced into the sheath and advanced to the desired position. Lastly, the sheath is removed, leaving the device disposed within the blood vessel.

It is known to configure an introducer sheath so that it may be easily removed or separated from the lead or catheter after it has been put in place. For example, it is known to provide score lines in the wall of the sheath to enable the sheath to be peeled away, slit, or split open. Once the sheath has been removed and catheter has been put in place, therapeutic medical devices such as endocardial pacing/defibrillation leads may be introduced into the blood vessel through the catheter.

Once the sheath has been inserted into a blood vessel, it provides a passage for the free flow of blood. This may result in significant blood loss from a patient. The sheath also provides an open passage for the introduction of air into the blood vessel, which could cause an embolism in the vascular system of the patient. To overcome these problems, vascular introducers have been developed with hemostatic valves that prevent the free flow of blood through the introducer sheath.

Examples of such devices are disclosed in U.S. Pat. No. 4,798,594 to Hillstead, U.S. Pat. No. 5,125,904 to Lee and U.S. Pat. No. 5,409,463 to Thomas et al., the disclosures of which are incorporated herein by reference in their entireties. In each of these devices, the hemostatic valve is configured to create frictional resistance to the passage of therapeutic devices such as flexible cardiac leads. This makes introduction of a lead difficult and can actually cause damage to the lead.

There is a need for a hemostasis valve for a vascular introducer that effectively prevents the backflow of blood and other fluids while exhibiting lower insertion and extraction forces than prior-art hemostasis valves.

SUMMARY OF THE INVENTION

A hemostasis valve for a vascular introducer is disclosed which includes a valve body having a seal region with opposed first and second end surfaces and a central axis extending through the seal region perpendicular to the first and second end surfaces. The first end surface of the seal region has a first grouping of cut lines formed on the first end surface and extending radially outward from the central axis. The second end surface of the seal region has a second grouping of cut lines formed on the second end surface and extending radially outward from the central axis. The first circumferential grouping of intersecting cut lines is axially aligned with and angularly offset from the second circumferential grouping of cut lines. A pair of planar slits extend angularly away from each cut line in the first end surface, through the valve body, to a respective pair of oppositely adjacent cut lines in the second end surface.

To achieve the advantages and benefits of the subject invention, the first circumferential grouping of cut lines can be angularly off-set from the second circumferential grouping of cut lines by 30 degrees, and a pair of planar slits extend angularly away from each cut line in the first end surface, through the valve body, to a respective pair of oppositely adjacent cut lines in the second end surface. This construct forms a valve opening defined by a series of intersecting geometric planes that serve to provide a complete hemostatic seal about an object introduced through the valve opening regardless of the diameter of the object, while exhibiting lower insertion and extraction forces than prior art hemostasis valves.

In one embodiment, a first diametrical parting line extends across the first end surface of the seal region. The first diametrical parting line intersects an aligned pair of cut lines formed in the first end surface of the seal region. The first diametrical parting line extends at least partially through the valve body toward the second end surface of the seal region. A second two-part diametrical parting line extends across the second end surface of the seal region. The second two-part diametrical parting line extends at least partially through the valve body toward the first end surface of the seal region.

In another embodiment, a first diametrical parting line extends partially across the first end surface of the seal region. The first diametrical parting line extends completely through the valve body from the first end surface to the second end surface. A second diametrical parting line partially extends from the first end surface to the second end surface at an angle of about 20 degrees to about 45 degrees.

These and other features of the hemostasis valve of the subject invention will become more readily apparent to those having ordinary skill in the art from the following detailed description of the invention taken in conjunction with the several drawings figures.

BRIEF DESCRIPTION OF THE DRAWINGS

So that those skilled in the art to which the subject invention belongs will readily understand how to make and use the hemostasis valve of the subject invention without undue experimentation, preferred embodiments of the hemostasis valve will be described in detail below with reference to certain figures, wherein:

FIG. 3 is a perspective view of the hemostasis valve of the subject invention, illustrating the upper surface of the valve;

FIG. 4 is a perspective view of the hemostasis valve of the subject invention, illustrating the lower surface of the valve;

FIG. 5 is a detailed view of the hemostasis valve of the subject invention, illustrating the upper surface cut lines of the valve;

FIG. 6 is a detailed view of the hemostasis valve of the subject invention, illustrating the lower surface cut lines of the valve;

FIG. 13 is a perspective view of the hemostasis valve of the subject invention, illustrating the upper surface of the valve for a splittable introducer;

FIG. 14 is a perspective cross-sectional view of the hemostasis valve of the subject invention taken along line 14-14 of FIG. 13, which is the central parting line of the valve;

FIG. 15 is a detailed perspective cross-sectional view of the hemostasis valve of the subject invention taken from a portion of the area 15 shown in FIG. 14, illustrating the valve surface material;

FIG. 16 is a perspective view of the hemostasis valve of the subject invention, illustrating the internal cut lines in the valve;

DETAILED DESCRIPTION

Figures 1, 2:
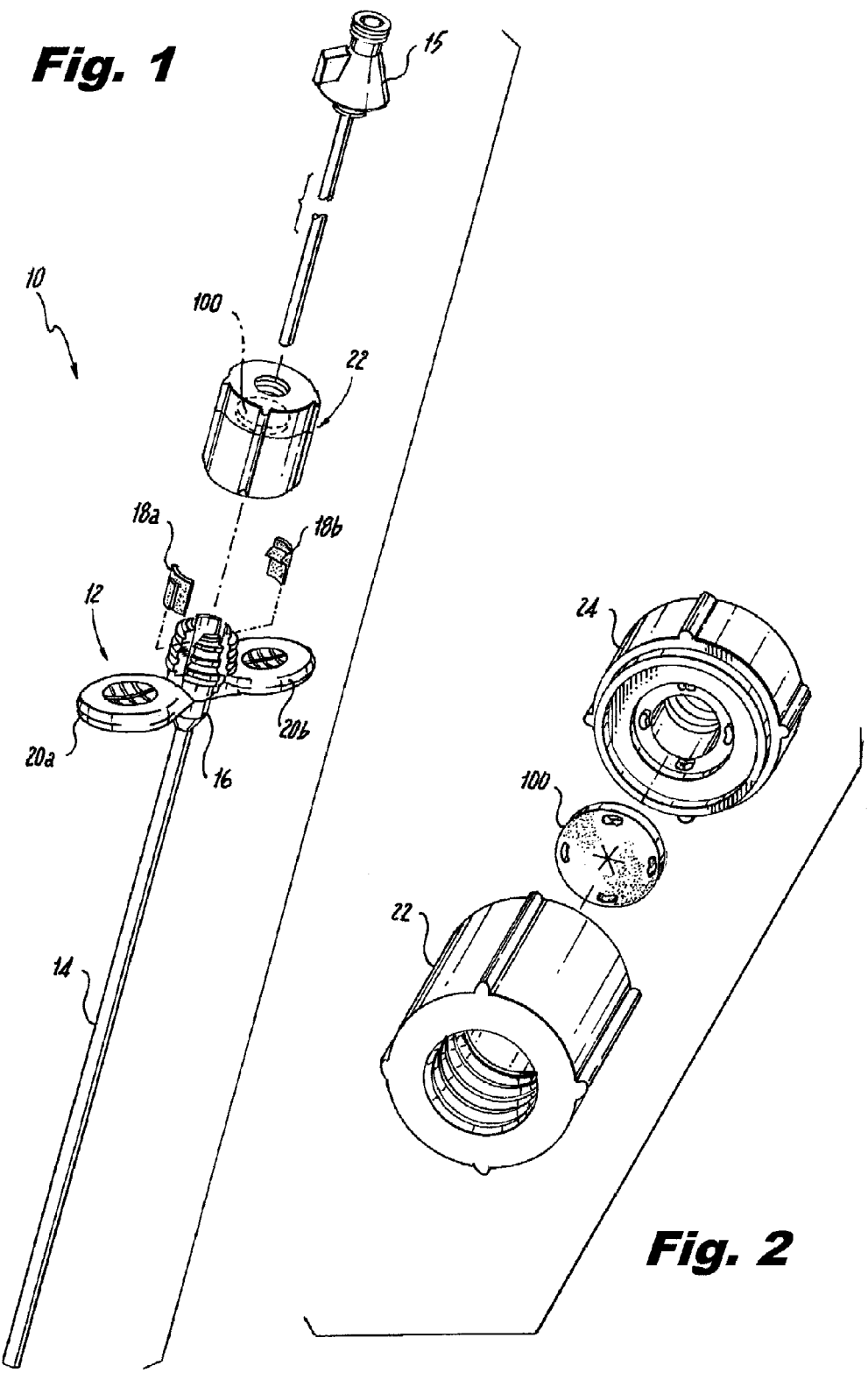
FIG. 1 is an exploded perspective view of a vascular introducer with parts separated for ease of illustration, including the hemostasis valve of the subject invention.
FIG. 2 is an enlarged perspective view of the hemostasis valve of the subject invention, illustrating placement of the valve within the body of an introducer housing.

Referring now to the drawings wherein like reference numerals identify similar structural features or aspects of the surgical devices disclosed herein, there is illustrated in FIG. 1 an exemplary embodiment of a splittable or peel-away vascular introducer designated generally by reference numeral 10, which includes the novel hemostasis valve of the subject invention.

Vascular introducer 10 is disclosed in U.S. Patent Application Publication 2008/0097386, which is incorporated herein by reference in its entirety for purposes of enablement and illustration. Those skilled in the art should readily appreciate that the disclosure of vascular introducer 10 should not be construed as limiting the scope of the subject invention in any way. In other words, while the hemostasis valve of the subject invention can certainly be employed with the exemplary vascular introducer 10, it can also be employed with other types of vascular introducers, including those which are not designed to be split in half or peeled away, as well as other types of surgical devices, such as cannulae or trocars in which a hemostatic valve can be employed to prevent the backflow of blood and other fluids.

FIG. 1 shows a vascular introducer 10 that includes a handle portion 12 and a distally extending tubular sheath 14 defining a central lumen for accommodating an elongated stylet 15. The handle portion 12 includes a central hub 16 that houses a two-part cylindrical seal assembly 18a, 18b and a pair of handle members 20a, 20b that extend radially from the central hub 16. An actuation cap 22 is operatively associated with the central hub 16 for effectuating movement of the seal assembly 18a, 18b between an open position in which the stylet 15 can pass freely through the central hub 16 and into the lumen of sheath 14, and a closed position in which the seal assembly 18a, 18b is inwardly compressed and tightly engaged around the stylet 15.

In one exemplary embodiment, a hemostasis valve member 100 is accommodated within the actuation cap 22 to prevent the backflow of blood or other fluids through the introducer, while preventing the ingress of air and contaminants into the introducer. As disclosed in more detail below, the unique construction of the hemostasis valve 100 provides a complete hermetic seal regardless of the size of the object that is introduced through the valve opening. That is, a completely hermetic seal is maintained, regardless of whether it is the stylet 15, a smaller diameter guidewire, or a larger diameter catheter that is passed through the valve opening.

FIG. 2 illustrates an exemplary embodiment of a hemostasis valve member of the present invention, designated generally by the reference numeral 100. As shown, valve member 100 is accommodated within the actuation cap 22 and an actuation body 24 of introducer 10.

FIGS. 3 and 4 show an exemplary embodiment of hemostasis valve member 100, which includes a valve body 110 with a planar upper surface 115, shown in FIG. 3, and a planar lower surface 116, shown in FIG. 4. In the exemplary embodiment shown, valve body 110 is cylindrical in shape, with upper surface 115 and lower surface 116 being positioned substantially parallel to one another and spaced apart by a predetermined distance.

As shown in FIGS. 3 and 4, valve body 110 includes a generally cylindrical and centrally located seal region 112 extending through valve body 110 from upper surface 115 to lower surface 116. In the exemplary embodiment shown, seal region 112 is centered at the intersection of a central axis x and a lateral axis y, as shown in FIG. 3. Central axis x extends through the center of valve body 110 and is perpendicular to upper surface 115 and lower surface 116. Lateral axis y intersects central axis x and is parallel to upper surface 115 and lower surface 116. In addition fixturing apertures 160 are formed in valve body 110, radially outward of seal region 112, for securing the valve body 110 within the actuation cap or another portion of a similar vascular introducer.

As shown in FIG. 3, upper surface 115 of seal region 112 may include a plurality of cut lines formed on the surface. In the exemplary embodiment shown, upper surface 115 includes a first grouping of six cut lines 120a-120f. Cut lines 120a-120f extend radially outward from the center of seal region 112 and are equidistantly spaced apart.

FIG. 4 illustrates a second grouping of cut lines 130a-130f formed on lower surface 116 of seal region 112. Cut lines 130a-130f also extend radially outward from the center of seal region 112 and are equidistantly spaced apart. However, cut lines 130a-130f are angularly offset from cut lines 120a-120f, such that the cut lines on upper surface 115 are not aligned with the cut lines on lower surface 116.

FIG. 5 is a detailed view taken from FIG. 3, showing the angle between cut lines 120a-120f that form a part of seal region 112. As shown, cut lines 120a-120f may extend radially outward from the center of seal region 112, be of equal length, and be equidistantly spaced apart. In other words, each of the individual cut lines that make up the first grouping of cut lines are separated from one another by an angle β, as shown in FIG. 5. In the exemplary embodiment shown, the first grouping of cut lines, formed on upper surface 115, includes six cut lines, with each cut line being spaced apart 60 degrees from the two adjacent cut lines. The configuration of the second grouping of cut lines on lower surface 116 is the same as the configuration of the first grouping of cut lines on upper surface 115, although the second grouping of cut lines is offset from the first grouping of cut lines.

FIG. 6 is a detailed view of lower surface 116 taken from FIG. 4, showing the second grouping of cut lines 130a-130f formed on lower surface 116. In FIG. 6, the first grouping of cut lines 120a-120f is shown in phantom, illustrating the offset angle α between the first grouping of cut lines 120a-120f formed on upper surface 115 and the second grouping of cut lines 130a-130f formed on lower surface 116. As shown, the first grouping of cut lines 120a-120f and the second grouping of cut lines are similarly configured, except that cut lines 130a-130f are rotated about central axis x such that, when both groupings of cut lines are projected onto a single plane, an offset angle α is formed between each of the cut lines in the first grouping and the adjacent cut lines from the second grouping. In one exemplary embodiment, offset angle α is approximately 30 degrees.

The configuration of cut lines described above creates a plurality of intersecting planar slits defining a valve opening that provides a completely hemostatic seal with an object introduced through the valve, regardless of the diameter of the object, while exhibiting lower insertion and extraction forces than prior-art hemostasis valves.

As shown in phantom in FIGS. 3 and 4, a pair of planar slits extend angularly away from each cut line in upper surface 115, through the valve body 110, to a respective pair of oppositely adjacent, equidistantly spaced apart cut lines in the lower surface 116. More particularly, planar slits extend from cut line 120a in the upper surface 115 to oppositely adjacent cut lines 130a and 130f in the lower surface 116; planar slits extend from cut line 120b in the upper surface 115 to oppositely adjacent cut lines 130a and 130b in the lower surface 116; planar slits extend from cut line 120c in the upper surface 115 to oppositely adjacent cut lines 130b and 130c in the lower surface 116; planar slits extend from cut line 120d in the upper surface 115 to oppositely adjacent cut lines 130c and 130d in the lower surface 116; planar slits extend from cut line 120e in the upper surface 115 to oppositely adjacent cut lines 130d and 130e in the lower surface 116; and planar slits extend from cut line 120f in the upper surface 115 to oppositely adjacent cut lines 130e and 130f in the lower surface 116.

Figure 7:
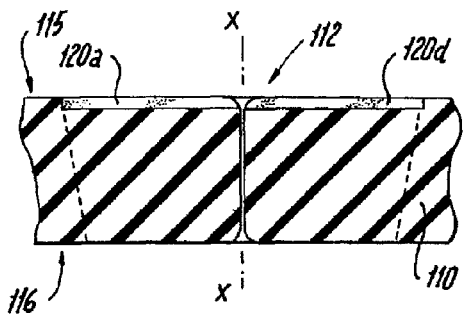
FIG. 7 is a detailed cross-sectional view of the hemostasis valve of the subject invention taken along line 7-7 of FIG. 3, illustrating one view of the slit pattern.

FIG. 7 is a partial cross-sectional view of the hemostasis valve 100 taken along line 7-7 of FIG. 3, illustrating a vertical center cut through the valve body 110 along the central axis x, with the planar slits which extend from cut lines 120a, 120d shown in phantom.

Figure 8:
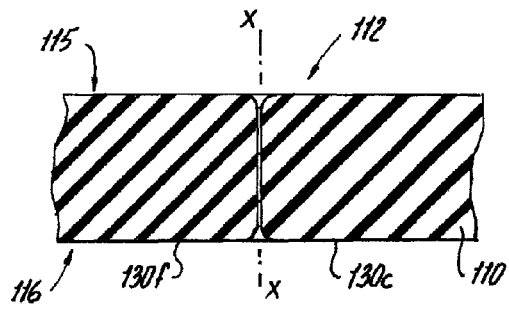
FIG. 8 is a partial cross-sectional view of the hemostasis valve of the subject invention taken along line 8-8 of FIG. 3, illustrating the center cut of the valve.

FIG. 8 is a partial cross-sectional view of the hemostasis valve 100 taken along line 8-8 of FIG. 3, illustrating a vertical center cut through the valve body 110 along the central axis x and a view of the valve body 110 material along the cut lines 130c and 130f.

Figure 9:
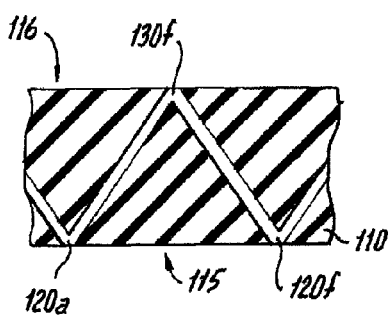
FIG. 9 is a partial cross-sectional view of the hemostasis valve of the subject invention taken along line 9-9 of FIG. 4, illustrating the planar cut line pattern through the valve.

FIG. 9 is a partial cross-sectional view of the hemostasis valve 100 taken along line 9-9 of FIG. 4, illustrating the planar slits which extend from cut line 120a to cut line 130f and from cut line 120f to cut line 130f. As shown, the planar slits are disposed at an angle with respect to upper surface 115 and lower surface 116.

Figure 10:
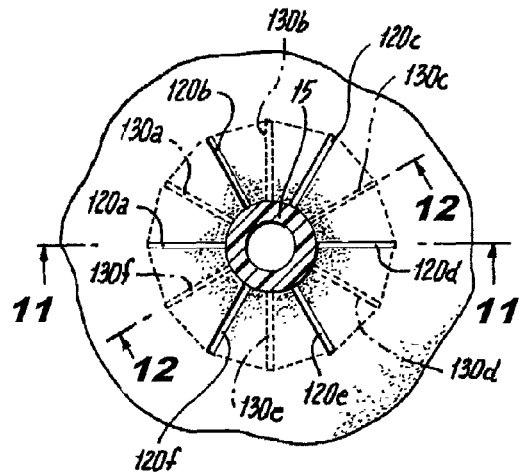
FIG. 10. is a partial top view of the hemostasis valve of the subject invention, illustrating a catheter passing through the hemostasis valve.
Figure 11:
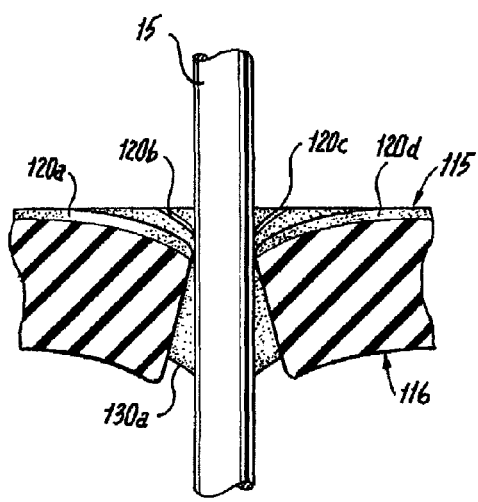
FIG. 11 is a partial cross-sectional view of the hemostasis valve of the subject invention taken along line 11-11 of FIG. 10, illustrating an elongated stylet passing through the hemostasis valve.
Figure 12:
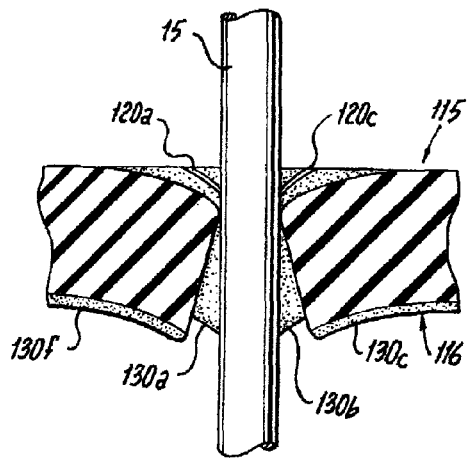
FIG. 12 is an elevational cross-sectional view of the hemostasis valve of the subject invention taken along line 12-12 of FIG. 10, illustrating a catheter passed through the hemostasis valve.
Figure 17:
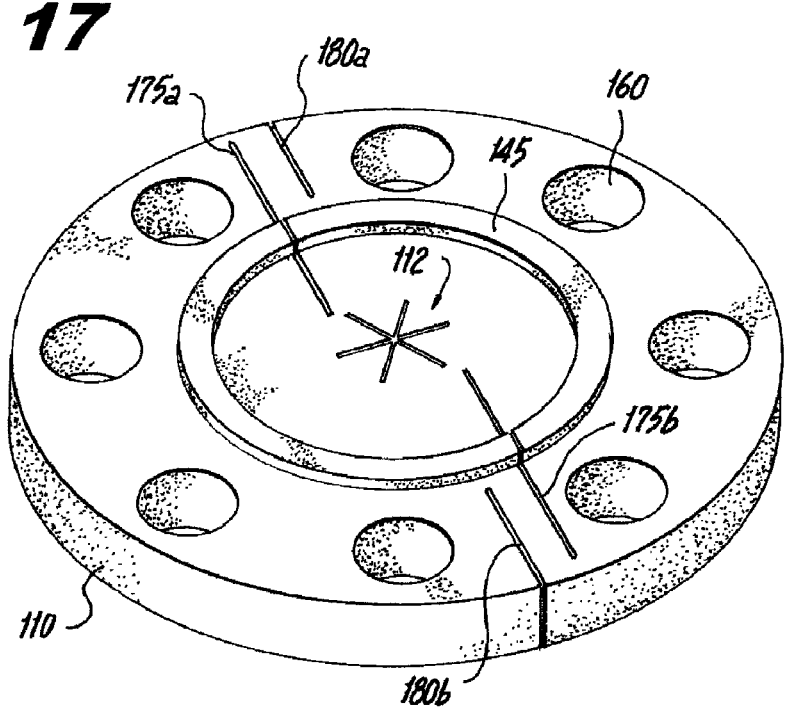
FIG. 17 is a perspective view of the hemostasis valve of the subject invention, illustrating the upper surface of the valve for a splittable introducer.
Figure 18:
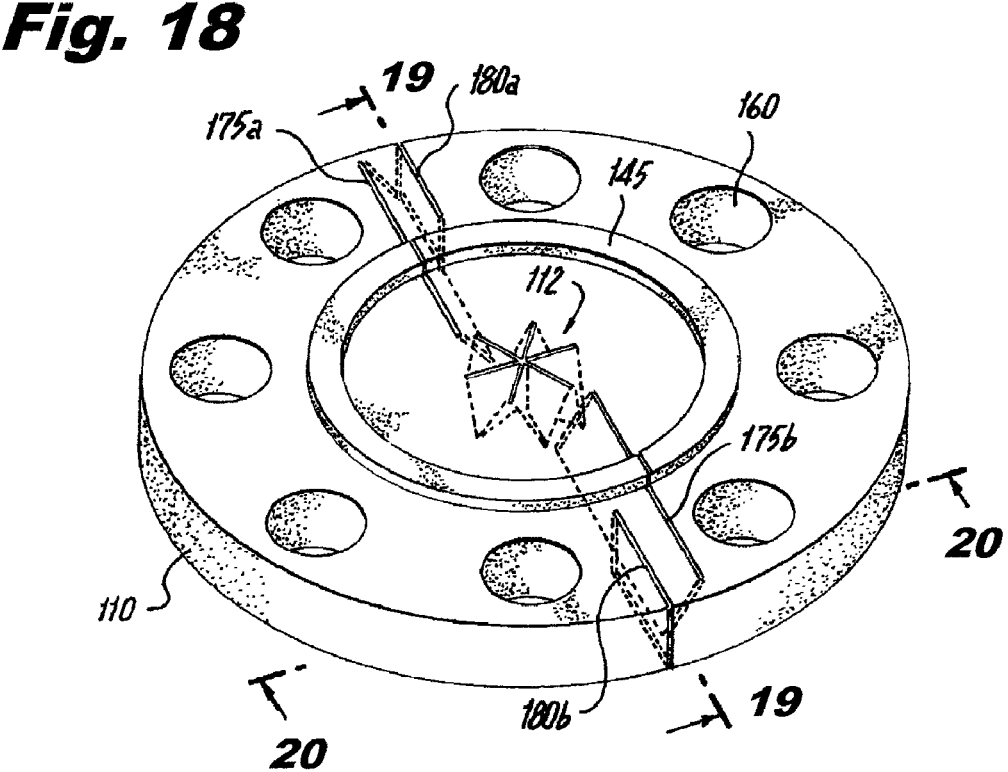
FIG. 18 is a perspective view of the hemostasis valve of the subject invention, illustrating the internal cut lines in the valve.

FIGS. 10-12 illustrate an exemplary embodiment of hemostasis valve member 100, with an elongated stylet 15 passing through the valve. The combination of planar slits between the cut lines 120a-120f and 130a-130f (shown in phantom) allows easy introduction and removal of the stylet 15 of varying circumference while maintaining a hermetic seal.

As mentioned above, hemostasis valve 100 can be employed with a splittable or a non-splittable introducer. For instance, where the valve member 100 is associated with a splittable introducer, it is configured to be spilt in half. In this regard, in one exemplary embodiment as shown in FIGS. 13-16, valve body 112 includes a first diametrical parting line 140 that intersects the aligned pair of cut lines 120a, 120d formed in the upper surface 115 of seal region 112. The first diametrical parting line 140 extends partially through valve body 112 toward the lower surface 116 of seal region 112. A second two-part diametrical parting line 150a, 150b extends across the lower surface 116 of seal region 112 and partially through the valve body 110 toward the upper surface 115 of seal region 112. A portion of the valve body 110 is left uncut as a break membrane 170. The break membrane 170 is configured to hold the two halves of the valve body 110 together and maintain a hermetic seal until the splittable introducer is pulled apart.

As best seen in FIG. 13, the upper surface 115 of seal region 112 is circumscribed by a stepped seal ring 145 for cooperating with structural aspects of the actuation cap with which the valve is associated. In addition, as shown in FIGS. 13-16, fixturing apertures 160 are formed in valve body 110, radially outward of seal region 112, for securing the valve body 110 within the actuation cap or another portion of a similar vascular introducer.

FIGS. 17-20 illustrate another exemplary embodiment of valve member 100. In this exemplary embodiment, valve body 112 includes a first two-part diametrical parting line 180a, 180b cut perpendicular to the upper surface 115 which does not extend into the seal region 112. The first two-part diametrical parting line 180a, 180b extends completely through valve body 110 from the upper surface 115 through to the lower surface 116. A second two-part diametrical parting line 175a, 175b partially extends from the upper surface 115 towards the lower surface 116 of seal region 112 at an angle γ with respect to the diametrical parting line 180a, 180b, as shown, for example, in FIG. 20. Angle γ can be any suitable angle. In one exemplary embodiment, angle γ is between about 20 degrees and about 45 degrees.

Figure 19:
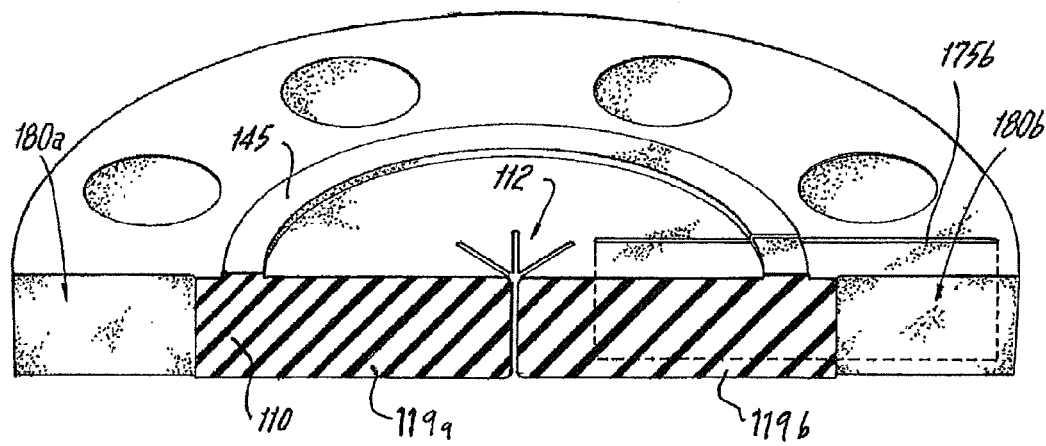
FIG. 19 is a perspective cross-sectional view of the hemostasis valve of the subject invention taken along line 19-19 of FIG. 18, illustrating the parting line of the valve.
Figure 20:
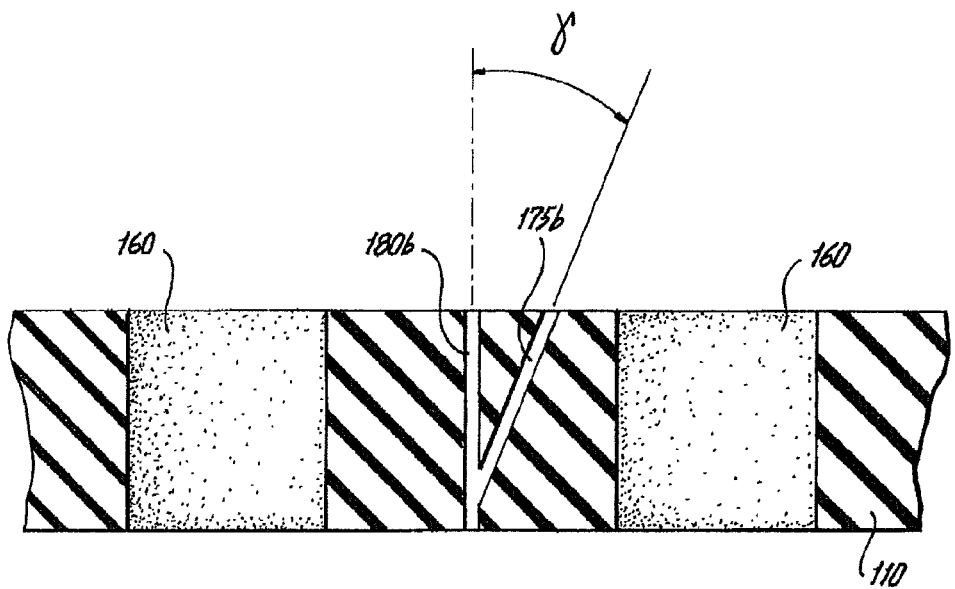
FIG. 20 is a side cross-sectional view of the hemostasis valve of the subject invention taken along line 20-20 of FIG. 18, illustrating the parting line of the valve.

As shown in FIG. 19, a portion of the valve body 110 is left uncut as a break membrane 190a, 190b. The break membrane 190a, 190b is configured to hold the two halves of the valve body 110 together and maintain a hermetic seal until the splittable introducer is pulled apart. The break membrane 190a, 190b is formed by the partial angular cuts of the second two part diametrical parting line 175a, 175b. In one exemplary embodiment, circular fixturing apertures 160 are formed near the stepped seal ring 145 with an area of valve body 110 outboard of the fixturing apertures 160. In one exemplary embodiment, the thickness of the break membrane 190a, 190b is chosen to provide a tear force no greater than one-half the force required to tear the fixturing apertures 160.

The valve body 110 is preferably formed from a silicone based polymeric material. It is envisioned that the silicone based polymeric material can include a filler. For example, the valve body 10 can be formed from a silicone matrix consisting of about 20 to 30 durometer silicone or a similar material, with a mixture of less than about 5% titanium dioxide or a similar material as a filler. The function of the valve is not dependant on the selection of a filler.

The embodiments of the valve member described above are exemplary and do not limit the invention in any way. Relative terms such as "upper" and "lower" have been included for ease of description only and should not be interpreted as limiting the invention. Those skilled in the art will readily appreciate that many changes may be made to the described embodiments without departing from the scope of the subject invention as defined by the appended claims.

What is claimed is:

1. A hemostasis valve for a vascular introducer comprising:
    a valve body having a seal region with opposed first and second end surfaces and a central axis extending through the seal region perpendicular to the first and second end surfaces, the first end surface of the seal region having a first grouping of cut lines formed on the first end surface and extending radially outward from the central axis, the second end surface of the seal region having a second grouping of cut lines formed on the second end surface and extending radially outward from the central axis;
    wherein the first grouping of cut lines is axially aligned with and angularly offset from the second grouping of cut lines; and
    wherein a pair of planar slits extend angularly away from each cut line in the first end surface, through the valve body, to a respective pair of oppositely adjacent cut lines in the second end surface.

2. A hemostasis valve as recited in claim 1, wherein the first and second grouping of cut lines are equidistantly spaced apart cut lines.

3. A hemostasis valve as recited in claim 1, wherein the first and second groupings of cut lines each include six cut lines.

4. A hemostasis valve as recited in claim 1, wherein the first grouping of cut lines is angularly offset from the second grouping of cut lines by 30 degrees.

5. A hemostasis valve as recited in claim 1, wherein a first diametrical parting line extends partially across the first end surface.

6. A hemostasis valve as recited in claim 1, wherein fixturing apertures are formed in the valve body radially outward of the seal region for securing the valve body within a valve housing.

7. A hemostasis valve as recited in claim 1, wherein the valve body is formed from a silicone based material.

8. A hemostasis valve as recited in claim 1, wherein the seal region of the first end surface is circumscribed by a raised seal ring.

9. A hemostasis valve as recited in claim 8, wherein a second diametrical parting line partially extends from the first end surface to the second end surface at an angle of about 20 degrees to about 45 degrees.

10. A hemostasis valve as recited in claim 1, wherein a first diametrical parting line extends across the first end surface of the seal region.

11. A hemostasis valve as recited in claim 10, wherein the first diametrical parting line extends at least partially through the valve body toward the second end surface of the seal region.

12. A hemostasis valve as recited in claim 11, wherein a first diametrical parting line extends completely through the valve body from the first end surface to the second end surface.

13. A hemostasis valve as recited in claim 10, wherein the first diametrical parting line intersects an aligned pair of cut lines formed in the first end surface of the seal region.

14. A hemostasis valve as recited in claim 13, wherein a second diametrical parting line extends at least partially across the second end surface of the seal region.

15. A hemostasis valve as recited in claim 13, wherein the second diametrical parting line extends at least partially through the valve body toward the first end surface of the seal region.

* * * * *